United States Patent [19]

Buhring et al.

[11] Patent Number: 5,763,274
[45] Date of Patent: Jun. 9, 1998

[54] ANTIBODY 103B2

[75] Inventors: Hans-Jorg Buhring, Tubingen, Germany; Andrew Zannettino, Highbury; Paul J. Simmons, Adelaide, both of Australia

[73] Assignee: Eberhard-Karls-Universität Tübingen, Tübingen, Germany

[21] Appl. No.: 689,941

[22] Filed: Aug. 16, 1996

[30] Foreign Application Priority Data

Aug. 17, 1995 [DE] Germany ............... 195 30 272.9

[51] Int. Cl.$^6$ ............... C12N 5/20; C12N 5/12; C07K 16/30; C07K 16/28

[52] U.S. Cl. ............... 435/344.1; 435/332; 435/334; 435/343; 435/344; 435/330; 435/346; 530/388.2; 530/388.22; 530/387.7; 530/388.7; 530/388.8; 530/388.85; 530/389.6; 530/809; 935/89; 935/104

[58] Field of Search ............... 424/143.1, 152.1, 424/153.1, 155.1, 156.1, 173.1, 174.1, 172.1, 178.1, 183.1, 1.49; 435/7.1, 7.2, 7.21, 7.23, 334, 343, 344.1, 70.21, 332, 330, 344, 346; 530/388.22, 388.7, 388.8, 388.85, 389.6, 391.1, 391.3, 391.7, 809, 388.2, 387.7; 935/89, 104, 107

[56] References Cited

PUBLICATIONS

Masuzawa et al., J. Biochem., 112:609–615, 1992.

Zannettino et al., Blood, vol. 86, (10 Suppl. 1), 591A, 1995.

Buhring et al., Blood, vol. 86, (10 Suppl. 1), 659A, 1995.

Harris et al., Tibtech, 11:42–44, 1993.

Waldmann, Science, 252:1657–1662, 1991.

*Primary Examiner*—Ronald B. Schwadron
*Attorney, Agent, or Firm*—Claude A. S. Hamrick

[57] ABSTRACT

An antibody against peanut agglutinin-(PNA)-binding glycoprotein on the surface of cells is named 103B2 and registered at the German Collection of Microorganisms and Cell Cultures GmbH, DSMZ, under the Budapest Treaty.

2 Claims, 1 Drawing Sheet

ANTIBODY 103B2

The invention relates to an antibody against peanut agglutinin(PNA)-binding glycoprotein on the surfaces of cells.

Malignant cells in a number of human tumors have peanut agglutinin(PNA)-binding glycoproteins on their surface. These PNA-binding glycoproteins offer the possibility of bringing detection reagents and/or therapeutically effective reagents directly onto the corresponding cells and of binding these to them. The glycoproteins MUC1, MUC2 and MUC3, named after the MUC nomenclature which has in the meantime been introduced, have been known for a number of years. A recently identified cell surface glycoprotein is the protein MGC-24, whose amino acid sequence and corresponding nucleotide sequence have been fully identified by Masuzawa et. al., J. BIOCHEM. 112, 609–615 (1992). This glycoprotein MGC-24 is thus ideally suited as a target point for a specific cellular diagnosis or therapy.

An antibody which binds specifically to this glycoprotein MGC-24 could be a possible mediator for a corresponding, target-specific cellular diagnostic or therapeutic agent.

Such an antibody can be linked to both simple detection reagents such as fluorescent dyes or radioactive materials as well as special, therapeutically-effective reagents.

However, as yet only a polyclonal antibody, which thus has limited availability and cannot be identically reproduced, is known. Moreover this is directed against a modified, namely deglycosylated form of the MGC-24 protein.

A specific treatment and identification of cells carrying MGC-24, among others in living organisms, is thus impossible with such an antibody.

The object of the present invention is thus to provide an antibody which binds specifically to the native, unmodified peanut agglutinin(PNA)-binding cell surface glycoprotein MGC-24 and which is available in practically unlimited quantities.

This object is achieved by the provision of a monoclonal antibody which binds specifically to the native, unmodified peanut agglutinin (PNA) -binding cell surface glycoprotein MGC-24. Such a monoclonal antibody is produced and released by hybridoma cells registered under the Budapest Treaty at the German Collection of Microorganisms and Cell Cultures GmbH, DSMZ, under the number DSM ACC 2221. It is known by the name 103B2. The date of deposition is August 1, 1995.

A further monoclonal antibody which binds specifically to the native, unmodified peanut agglutinin (PNA) -binding cell surface glycoprotein MGC-24, though on a different epitope, is produced and released by hybridoma cells registered at the German Collection of Microorganisms and Cell Cultures GmbH, DSMZ, under the number DSM ACC 2222. This is known by the name 105A5. This antibody is the subject matter of parallel German patent application DE 195 30 273.7 "Antibody 105A5".

With the antibody in accordance with the invention and the antibody from the parallel patent application in each case a monoclonal antibody was provided for the first time which can be reproduced in a standard form and which can thus be manufactured in potentially unlimited quantities and which binds specifically to a special epitope on the cell surface glycoprotein MGC-24.

The antibody in accordance with the invention enables a specific identification and influence of cells which express an extra-cellular domain of this protein MGC-24. It thus represents an as yet unique and versatile means for physicians and scientists of on the one hand identifying such cells, both in the cell culture and patient organism, and on the other of possibly manipulating these cells, either through antibody itself or through the specific reagents which are linked to the latter.

The invention furthermore relates to hybridoma cells which produce a monoclonal antibody against the protein MGC-24. These include in particular hybridoma cells registered under the Budapest Treaty at the German Collection of Microorganisms and Cell Cultures GmbH, DSMZ, under the number DSM ACC 2221 and producing the antibody called 103B2.

In addition the invention relates to a method of producing hybridoma cells which synthesize and release an antibody to the native, unmodified cell surface glycoprotein MGC-24. This method consists of the essentially familiar steps as described, for example, by Buhring et. al. in Hybridoma 1991, Volume 10, No. 1, P. 77–78:

1. immunization or sensitization of an animal, preferably a mouse from Balb/c stock, with the antigen or immunogen;

2. extraction of the antibody-producing cells, preferably the splenic lymphocytes of this animal;

3. fusion of these antibody-producing cells with a stable, immortalized cell line, preferably a myeloma cell line, to hybridoma cells; and 4. isolation and multiplication (cloning) of such hybridoma cells which secrete an antibody which binds to the antigen.

The method in accordance with the invention is characterized by the fact that the animal is immunized with cells from the undifferentiated, megakaryoblastoid cell line MOLM-1.

The advantage of this is that this cell line displays a strong expression of MGC-24, as could be shown during the tests leading to the antibody 103B2.

When screening for hybridoma cells which produce stem cell-specific antibodies, it is preferred during isolation of the hybridoma cells if those hybridoma cells are selected which produce antibodies with a specificity against bone marrow cells, it being further preferred if only those hybridoma cells are tested for the specificity of the antibodies which they produce against bone marrow cells, for which hybridoma cells it has already been proven that their antibodies have only a weak or preferably negative reaction with peripheral blood cells.

The advantage of this is that it enables a rapid screening without a number of cells having to be tested in vain. It was surprisingly discovered that MGC-24 is also expressed on stem cells, so that during screening the fact can be exploited that a large number of undifferentiated cells including hematopoietic stem cells which express the antigen recognized by the antibody are present in the marrow. Antibodies which bind selectively to antigens on bone marrow cells and do not or only weakly bind on peripheral blood cells can thus be easily isolated through a preliminary test for a reaction with peripheral blood cells. In other words, the specificity during selection is hereby greatly increased by a simple means.

The invention also relates to the use of a monoclonal antibody against the cell surface glycoprotein MGC-24 for a diagnostic and/or therapeutic treatment of tumors, in particular gastric and colon carcinoma.

Tumor cells, in particular gastric and colon carcinoma cells, are characterized by a relatively high content of cell surface glycoprotein MGC-24. An antibody in accordance with the invention which is conjugated with an indicator, for example a radioactive marker, binds this indicator indirectly to these cells thus enabling the direct identification of these cells, for example, by X-ray diagnosis or scintigram. This permits a very early in vivo tumor diagnosis in certain cases.

The antibody can be conjugated with a therapeutically effective agent in a suitable manner, thus enabling a direct and specific influence or even elimination of cells carrying MGC-24, in particular tumor cells.

In a preferred embodiment an antibody produced and released by the hybridoma cells registered at the German Collection of Microorganisms and Cell Cultures GmbH, DSM, under the number DSM ACC 2221 is used for such a diagnostic and/or therapeutic treatment.

In order to facilitate the therapeutic and/or diagnostic application of the antibody in accordance with the invention, the antibody can be mixed with suitable auxiliary ingredients to obtain a pharmaceutical preparation. The invention thus also relates to a pharmaceutical agent for the diagnostic and/or therapeutic treatment of tumors which contains an antibody in accordance with the invention which binds to the cell surface glycoprotein MGC-24. This pharmaceutical agent preferably contains an antibody produced and released by the hybridoma cells registered at the German Collection of Microorganisms and Cell Cultures GmbH, DSMZ, Mascheroder Weg 10, D-38124 Braunschweig, under the number DSM ACC 2221.

Using an antibody in accordance with the invention, cells carrying MGC-24 can be identified in a suspension of various cells using familiar contemporary test methods, for example enzyme-linked-immunosorbet-assay, or ELISA for short, or radioimmunoassay, RIA. The present invention thus also relates to a kit to identify the peanut monoclonal antibody, which binds specifically to the native glycoprotein MGC-24.

A preferred embodiment of this kit is characterized by the fact that the kit comprises an antibody produced by the hybridoma cells registered at the German Collection of Microorganisms and Cell Cultures GmbH, DSMZ, under the number DSM ACC 2221.

In connection with the present invention it could surprisingly be shown—as mentioned before—that the monoclonal antibody named 103B2 produced by the hybridoma cells registered at the German Collection of Microorganisms and Cell Cultures GmbH, DSMZ, under the number DSM ACC 2221, binds to stem cells.

The invention thus also relates to the use of an antibody in accordance with the invention, preferably the antibody 103B2, to identify hematopoietic cells and a kit to identify hematopoietic cells which contains an antibody in accordance with the invention, preferably the antibody 103B2. It is hereby possible to fractionate undifferentiated CD 34+ sub-populations and to select and purify cells from the erythroidal line or the marrow for functional analyses.

A further surprising effect is that the addition of monoclonal antibody 103B2 to immature erythroid cells inhibits the in-vitro hematopoiesis.

The invention thus also relates to the use of an antibody in accordance with the invention, preferably the antibody 103B2, to inhibit hematopoiesis.

Further advantages can be taken from the following description.

It is understood that the aforementioned features and those to be explained in the following can be used not only in the specified combinations but also in other combinations or alone without going beyond the scope of the present invention.

The invention is explained in more detail in the following on the basis of application examples and embodiments with reference to the drawings, in which:

Example 1

Figure 1:
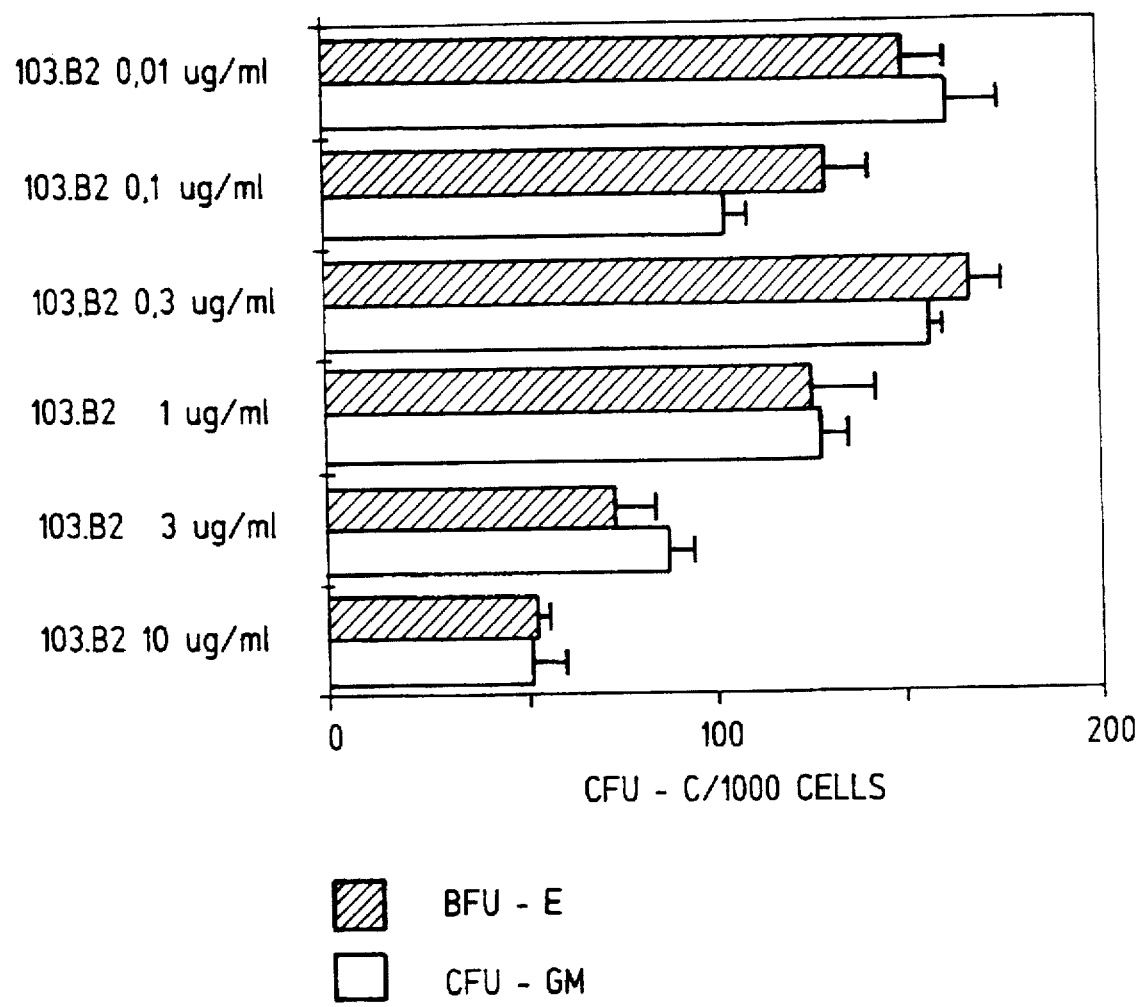
FIG. 1 is a bar chart showing the suppression of hematopoiesis by the antibody 103B2.

Production and characterization of monoclonal antibodies against the cell surface glycoprotein MGC-24

Cells from the undifferentiated, megakaryoblastoid cell line MOLM-1 are used as an antigen (Matsuo Y, Adachi, T, Tsubota T, Imanishi J, Minowada J. Establishment and characterization of a novel megakaryoblastoid cell line, MOLM-1, from a patient with chronic myelogenous leukaemia. Human Cell 1991; 4: 261–264).

Eight week-old Balb/c mice were injected intraperitoneally at intervals of 10 days with $10^7$ cells from cell line MOLM-1 for immunization. Four days before the fusion $5\times10^5$ cells were applied directly into the spleen to strengthen the immunologic response.

The production of antibodies in the mouse organism was tested by screening the blood serum of the affected animal for binding properties with the antigen using the ELISA test familiar to experts.

After approx. 3 weeks the lymphocytes of the successfully immunized animal were collected by surgically removing the spleen and triturating this to a cell suspension.

The suspended spleen cells were fusioned with myeloma cells from the known strain SP2/0 in the presence of polyethylene glycol. The fusion culture was cultivated in a medium containing hypoxanthine, aminopterine and thymidine (HAT medium), in this case HAT-RPMI-1640, in which only hybrid cells could grow since these have both the myeloid cell's property of unlimited division and the property of the lymphocytes, which produce the antibody, to grow in a medium containing HAT.

Following fusion the cells were plated-out in microtiter plates and incubated at 37° C., 5% $CO_2$.

The culture supernatants were screened after 10–14 days on the MOLM-1 cell line in a flow cytometer. In a second stage the supernatants were tested for a reaction with peripheral blood cells since these do not express specific stem cell antigens. Supernatants which displayed a negative or weak reaction with peripheral blood cells were then tested for their reaction with bone marrow cells. Hybridomas which produced antibodies with a specificity for bone marrow cells were selected, isolated and cultivated, i.e. cloned, according to the known limiting dilution method.

This screening strategy benefited from the fact that a large number of undifferentiated cells, including hematopoietic stem cells, occur in marrow.

Hybridoma cell cultures which displayed a positive reaction were cultivated further, the antibodies concentrated, purified and characterized.

The monoclonal antibody 103B2 was obtained at the end of the foregoing screening strategy. With the PE-conjugated anti-isotype-specific antiserum, the isotype was determined as IgG3 by means of direct immunofluorescence.

The production, purification and characterization of the antibodies was carried out using methods familiar to the man skilled in the art.

The antibody 103B2, produced by the hybridoma cell registered at the German Collection of Microorganisms and Cell Cultures GmbH, DSMZ, the number DSM ACC 2221, displays the following characteristic features:

Imunoglobulin class: IgG3
specific binding affinity to: MGC-24

Example 2

Identification of the antigen recognized by the monoclonal antibody 103B2

The antigen was identified with a stroma expression library.

A retro-viral expression library was constructed according to the method described by Rayner and Gonda in Mol. Cell. Biol. 1994, Volume 14, Page 880 to isolate the gene encoding the antigen recognized by the monoclonal antibody 103B2. mRNA from cultured stroma cells of human marrow was used in this method.

cDNA transcripts were directionally cloned in the retroviral plasmid vector pRUF.Neo. DNA from the library was used to transfect an amphotropic packaging cell line (PA317). Transiently generated retroviral particles were harvested and used for a stable infection of an ecotropic packaging cell line. Viruses produced from these cells were then used to infect the factordependent murinic hematopoietic cell line FDC-P1.

Infected FDC-P1 cells were selected for G418-resistance, and cells which express the antigen recognized by the antibody 103B2 were isolated and enriched. The enrichment of the cells recognized by the antibody was carried out using multiple rounds of an immuno-magnetic cell sorting (Dynabeads). Following this FACS sorting clonal populations of the transfected cells were established.

Proviral cDNA inserts were then recovered from genomic DNA of the infected cells. A PCR amplification was performed for this purpose whereby specific retroviral primers which flank the cloning site in the plasmid vector were employed. In this way it was possible to isolate a cDNA insert of approximately 3 kBp.

A sequence analysis showed that this insert identified a previously cloned gene from the mucin family, namely MGC-24, which was fully identified by Masuzawa et. al., J. Biochem. 112, 609–615 (1992).

Example 3

Use of the monoclonal antibody 103B2 to suppress in vitro hematopoiesis

The antibody's ability to disturb hematopoietic cell development was tested to investigate the function of the antigens identified by the monoclonal antibody 103B2.

In a first test purified monoclonal antibodies were added at incremental concentrations from 0.01–30 µg/ml to semi-solid clonogenic assays of human hematopoietic progenitors. These assays were performed using normal human bone marrow cells which express the CD-34 antigen. The purity of this cell population in all tests was 95–98.5%.

The CD34+ cells were cultured for 14 days at an initial concentration of 1000 cells per milliliter in IMDM which was supplemented by L-glutamine, penicillin, streptomycine, beta- mercaptoethanol, 0.9% (weight/volume) methyl cellulose, 1% bovine serum albumin, 30% (volume/volume) foetal calf serum and 10 ng/ml of the following, purified recombinant human cytokines: IL-1, IL-3, IL-6, G-CSF, GM-CSF, SCF and erythropoietin.

After 14 days the cultures were scored for the presence of colonies derived from the progenitors of myeloid cells (CFU-GM) or erythroid cells (BFU-E) in accordance with standard criteria. Compared with a binding (P4C2) and non-binding (AA6) control antibody of the same isotype IgG3, which was added in identical concentrations, the antibody 103B2 resulted in dose dependent inhibition of colony formation for both CFU-GM and BFU-E. The enclosed bar chart in FIG. 1 shows that at a concentration of 3 µg/ml antibody 103B2 the number of erythroid colonies was reduced by approx. 50% and at a concentration of 10 µg/ml by around 65% compared to the initial concentration.

Secondly the antibody was examined for the capacity to perturb hematopoiesis in stromal cell dependent long-term culture. The antibody 103B2 or a control antibody were added to cultures of myeloid stroma cells. These cultures were established from marrow obtained from normal donors. The cultured stromal cells were irradiated (1500 rad) to kill hematopoietic cells one week before the start of the experiment. The long-term culture was then established by adding $3 \times 10^4$ CD34+ cells per culture in the presence of the aforementioned antibody at a concentration of 10 µg/ml.

One week after adding the antibody a complete suppression of hematopoiesis in this system could be observed, evidenced through the complete absence of detectable hematopoietic progenitors and the death of the stromal cells.

We claim:

1. A monoclonal antibody, that is produced and released by hybridoma cells registered under the Budapest Treaty at the German Collection of Microorganisms and Cell Cultures GmbH DSMZ, Mascheroder Weg 10, D-38124 Braunschweig under the number DSM ACC 2221.

2. Hybridoma cells that are registered under the Budapest Treaty at the German Collection of Microorganisms and Cell Cultures GmbH DSMZ Mascheroder We 10, D-38124 Braunschweig, under the number DSM ACC 2221.

* * * * *